(12) United States Patent
Nycz et al.

(10) Patent No.: US 11,076,825 B2
(45) Date of Patent: Aug. 3, 2021

(54) SURGICAL INSTRUMENT TO ASSESS TISSUE CHARACTERISTICS (71) Applicant: WARSAW ORTHOPEDIC, INC., Warsaw, IN (US)

(72) Inventors: Jeffrey H. Nycz, Collierville, TN (US); Fred J. Molz, IV, Collierville, TN (US); Steven Tethrake, Collierville, TN (US); Stanley Warren Olson, Jr., Germantown, TN (US); William T. Donofrio, Andover, MN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 407 days.

(21) Appl. No.: 16/170,503

(22) Filed: Oct. 25, 2018

(65) Prior Publication Data
US 2019/0059849 A1 Feb. 28, 2019

Related U.S. Application Data (62) Division of application No. 14/955,985, filed on Dec. 1, 2015, now Pat. No. 10,111,646, and a division of
(Continued)

(51) Int. Cl.
*A61B 8/08* (2006.01)
*A61B 8/12* (2006.01)
*A61B 17/88* (2006.01)
*A61B 8/00* (2006.01)
*A61B 17/17* (2006.01)
(Continued)

(52) U.S. Cl.
CPC .............. *A61B 8/0875* (2013.01); *A61B 8/12* (2013.01); *A61B 8/4483* (2013.01); *A61B 8/483* (2013.01); *A61B 8/5223* (2013.01); *A61B 17/1703* (2013.01); *A61B 17/8805* (2013.01); *A61B 5/4504* (2013.01); *A61B 5/4509* (2013.01);
(Continued)

(58) Field of Classification Search
None
See application file for complete search history.

(56) References Cited

U.S. PATENT DOCUMENTS 4,246,791 A 1/1981 Glenn
4,669,482 A 6/1987 Ophir
(Continued)

FOREIGN PATENT DOCUMENTS

WO WO0230338 4/2002

OTHER PUBLICATIONS

Wikipedia contributors. Bone cyst [Internet], Wikipedia, The Free Encyclopedia, Oct. 21, 2016, 19:25 UTC [cited Apr. 1, 2017]. Available from: https://en.wikipedia.org/w/index.php?title=Bone_cyst&oldid=745545322.
(Continued)

*Primary Examiner* — Katherine L Fernandez (57) ABSTRACT

A surgical instrument for assessing tissue characteristics such as tissue density and volume is disclosed. The surgical instrument is hand-held and includes transducers adapted for emitting and/or receiving acoustic signals. The surgical instrument utilizes pulse-echo to determine tissue characteristics. The surgical instrument may be utilized to determine such things as the size of a lesion and whether the lesion has been completely removed or filled with graft material.

20 Claims, 2 Drawing Sheets

Related U.S. Application Data application No. 11/356,643, filed on Feb. 17, 2006, now abandoned.

(51) Int. Cl.
*A61B 5/00* (2006.01)
*A61B 17/56* (2006.01)

(52) U.S. Cl.
CPC ............ *A61B 8/4245* (2013.01); *A61B 8/4472* (2013.01); *A61B 17/56* (2013.01)

(56) References Cited

U.S. PATENT DOCUMENTS

| | | | |
|---|---|---|---|
| 4,672,963 A | 6/1987 | Barken | |
| 4,756,313 A | 7/1988 | Terwilliger | |
| 4,969,888 A | 11/1990 | Scholten | |
| 5,038,787 A | 8/1991 | Antich et al. | |
| 5,178,148 A | 1/1993 | Lacoste et al. | |
| 5,197,475 A | 3/1993 | Antich et al. | |
| 5,259,384 A * | 11/1993 | Kaufman | A61B 8/0875 128/925 |
| 5,284,148 A | 2/1994 | Dias et al. | |
| 5,306,306 A | 4/1994 | Bisek et al. | |
| 5,375,600 A | 12/1994 | Melton, Jr. | |
| 5,394,875 A | 3/1995 | Lewis et al. | |
| 5,402,781 A | 4/1995 | Dimarogonas | |
| 5,480,439 A | 1/1996 | Bisek et al. | |
| 5,564,423 A | 10/1996 | Mele et al. | |
| 5,590,658 A | 1/1997 | Chiang et al. | |
| 5,690,114 A | 11/1997 | Chiang et al. | |
| 5,749,363 A | 5/1998 | Ishii et al. | |
| 5,785,663 A | 7/1998 | Sarvazyan | |
| 5,836,876 A | 11/1998 | Dimarogonas | |
| 5,839,442 A | 11/1998 | Chiang et al. | |
| 5,852,647 A | 12/1998 | Schick et al. | |
| 5,855,563 A | 1/1999 | Kaplan et al. | |
| 5,891,033 A | 4/1999 | O'Neill et al. | |
| 5,928,239 A | 7/1999 | Mirza | |
| 5,957,846 A | 9/1999 | Chiang et al. | |
| 5,964,709 A | 10/1999 | Chiang et al. | |
| 6,034,296 A | 3/2000 | Elvin et al. | |
| 6,106,472 A | 8/2000 | Chiang et al. | |
| 6,109,112 A | 8/2000 | Borza et al. | |
| 6,122,538 A | 9/2000 | Sliwa et al. | |
| 6,200,266 B1 | 3/2001 | Shokrollahi et al. | |
| 6,230,036 B1 | 5/2001 | O'Neill et al. | |
| 6,235,038 B1 | 5/2001 | Hunter et al. | |
| 6,241,673 B1 | 6/2001 | Williams | |
| 6,364,849 B1 | 4/2002 | Wilcox | |
| 6,436,042 B1 | 8/2002 | Cadossi et al. | |
| 6,447,448 B1 | 9/2002 | Ishikawa et al. | |
| 6,500,119 B1 | 12/2002 | West et al. | |
| 6,500,487 B1 | 12/2002 | Holst et al. | |
| 6,529,127 B2 | 3/2003 | Townsend et al. | |
| 6,540,685 B1 | 4/2003 | Rhoads et al. | |
| 6,544,749 B1 | 4/2003 | Kim | |
| 6,585,647 B1 | 7/2003 | Winder | |
| 6,607,487 B2 | 8/2003 | Chang et al. | |
| 6,613,054 B2 | 9/2003 | Scribner et al. | |
| 6,676,291 B2 | 1/2004 | Ahn | |
| 6,692,450 B1 | 2/2004 | Coleman | |
| 6,719,692 B2 | 4/2004 | Kleffner et al. | |
| 6,733,458 B1 | 5/2004 | Steins et al. | |
| 6,751,492 B2 | 6/2004 | Ben-Haim | |
| 6,782,288 B2 | 8/2004 | Truwit et al. | |
| 6,881,214 B2 | 4/2005 | Cosman et al. | |
| 6,899,680 B2 | 5/2005 | Hoff et al. | |
| 6,980,419 B2 | 12/2005 | Smith et al. | |
| 7,108,696 B2 | 9/2006 | Daniel et al. | |
| 7,166,075 B2 | 1/2007 | Varghese et al. | |
| 7,419,487 B2 | 9/2008 | Johnson et al. | |
| 7,720,532 B2 | 5/2010 | Hashimshony et al. | |
| 7,744,607 B2 | 6/2010 | Wascher | |
| 7,806,892 B2 | 10/2010 | Makin et al. | |
| 7,833,221 B2 | 11/2010 | Voegele et al. | |
| 7,840,252 B2 | 11/2010 | Strommer et al. | |
| 2002/0103435 A1 | 8/2002 | Mault | |
| 2002/0133094 A1 | 9/2002 | Wilcox et al. | |
| 2003/0092977 A1 | 5/2003 | Sahatjian | |
| 2003/0167002 A1 | 9/2003 | Nagar et al. | |
| 2003/0220554 A1 | 11/2003 | Grenon et al. | |
| 2004/0054302 A1 | 3/2004 | Czernicki | |
| 2004/0138754 A1 | 7/2004 | Lang | |
| 2004/0143186 A1 | 7/2004 | Anisimov et al. | |
| 2004/0193048 A1 | 9/2004 | Tsoref | |
| 2004/0236221 A1 | 11/2004 | Wilcox et al. | |
| 2005/0015010 A1 | 1/2005 | Antich et al. | |
| 2005/0085725 A1 | 4/2005 | Nagar et al. | |
| 2005/0113691 A1 | 5/2005 | Liebschner | |
| 2005/0119587 A1 | 6/2005 | Roessler | |
| 2005/0197576 A1 | 9/2005 | Luo et al. | |
| 2005/0245803 A1 | 11/2005 | Glenn, Jr. et al. | |
| 2007/0021686 A1 | 1/2007 | Gellman | |
| 2007/0049821 A1* | 3/2007 | Willis | A61B 8/0883 600/437 |
| 2007/0150061 A1 | 6/2007 | Trieu | |

OTHER PUBLICATIONS

Wikipedia contributors. Phased array ultrasonics. Wikipedia, the Free Encyclopedia. Oct. 25, 2015, 23:09 UTC. Available at: https://en.wikipedia.org/w/index.php?title=Phased_array_ultrasonics&oldid=687494816. Accessed Oct. 28, 2015.

Barnett, Stanley B., et al. "The Sensitivity of Biological Tissue to Ultrasound," Ultrasound in Medicine and Biology, vol. 23, No. 6, pp. 805-812. World Federation for Ultrasound in Medicine and Biology, Jan. 1997.

European Patent Office, International Searching Authority, Notification of Transmittal of the International Search Report and the Written Opinion of the International Searching Authority or the Declaration, International Application No. PCT/US2007/062312, dated Jul. 5, 2007, 13 pages.

* cited by examiner

SURGICAL INSTRUMENT TO ASSESS TISSUE CHARACTERISTICS

The present application is a divisional of U.S. application Ser. No. 14/955,985, filed Dec. 1, 2015; which is a divisional of U.S. application Ser. No. 11/356,643, filed Feb. 17, 2006 (now abandoned); all of which are incorporated by reference herein.

FIELD OF THE INVENTION

The present invention is directed to improved instrumentation for assessing tissue characteristics and methods of using such instrumentation. More particularly, in one aspect the present invention is directed toward instruments and methods for assessing the size of a lesion.

BACKGROUND OF THE INVENTION

The present invention relates to the assessment of tissue density and related tissue characteristics. The assessment of tissue density is often required in orthopaedic procedures to evaluate the available treatment options and rehabilitation programs. Current techniques for treating lytic and cancerous lesions include debriding the lesion and filling the remaining defect with allograft materials. Advanced treatment options include the use of osteoinductive and osteoconductive materials to heal the lesion. These materials require accurate assessment of the lesion to ensure that the appropriate amount of biological agent is introduced into the lesion to promote rapid bone growth and healing. Typically, tissue assessments and lesion assessments are accomplished via radiographs, CT scans, or MRI scans followed by imaging techniques. However, these methods are expensive, time-consuming, and inconvenient.

Therefore, there remains a need for improved instruments and methods of treating lesions.

SUMMARY OF THE INVENTION

The present invention provides a surgical instrument that includes an energy source and a sensor for detecting reflected energy. A processor evaluates the reflected energy.

In another aspect, the present invention provides a surgical instrument for use in the treatment of a lesion of a bone. The surgical instrument includes a housing having an external gripping portion and a sensor portion having a conductive surface. In one aspect, the sensor portion is adapted to be in conductive contact with a lesion of a bone. The surgical instrument also includes an energy source adapted for emitting an energy signal into the lesion. The energy signal is configured to pass through the lesion and at least partially reflect off a boundary between the lesion and the adjacent tissue. The surgical instrument also includes a sensor adapted for detecting the reflected signal and a processor for determining the volume of the lesion based on the reflected signal.

In another aspect, the present invention provides a method of determining the size of a lesion of a tissue. The method includes placing an acoustic transducer in conductive contact with the lesion. The method also includes emitting an acoustic signal into the lesion. The acoustic signal is adapted to pass through the lesion and at least partially reflect off a boundary of the lesion adjacent the bone. The method also includes receiving at least a portion of the reflected signal and determining the volume of the lesion based on the portion of the reflected signal received.

In another aspect, the present invention provides a kit for treatment of a lesion of a bone. The kit includes a first container adapted for holding a first volume of bone void filler and a second container adapted for holding a second volume of bone void filler, and a hand-held ultrasonic device adapted for determining the volume of a lesion of a bone and indicating which of the first container or the second container corresponds to the volume of the lesion.

In yet a further aspect, a system and method are provided for sensing a lesion boundary and controlling lesion removal based on the sensed data. In one aspect, the lesion removal is computer controlled. In another aspect, lesion filling is computer controlled.

Further aspects, forms, embodiments, objects, features, benefits, and advantages of the present invention shall become apparent from the detailed drawings and descriptions provided herein. These and other objects of the present invention will be apparent from review of the following specification and the accompanying drawings.

DETAILED DESCRIPTION OF THE PREFERRED EMBODIMENT

For the purposes of promoting an understanding of the principles of the present invention, reference will now be made to the embodiments illustrated in the drawings, and specific language will be used to describe the same. It will nevertheless be understood that no limitation of the scope of the invention is intended. Any alterations and further modifications in the described devices, instruments, methods, and any further application of the principles of the invention as described herein are contemplated as would normally occur to one skilled in the art to which the invention relates.

Figure 1:
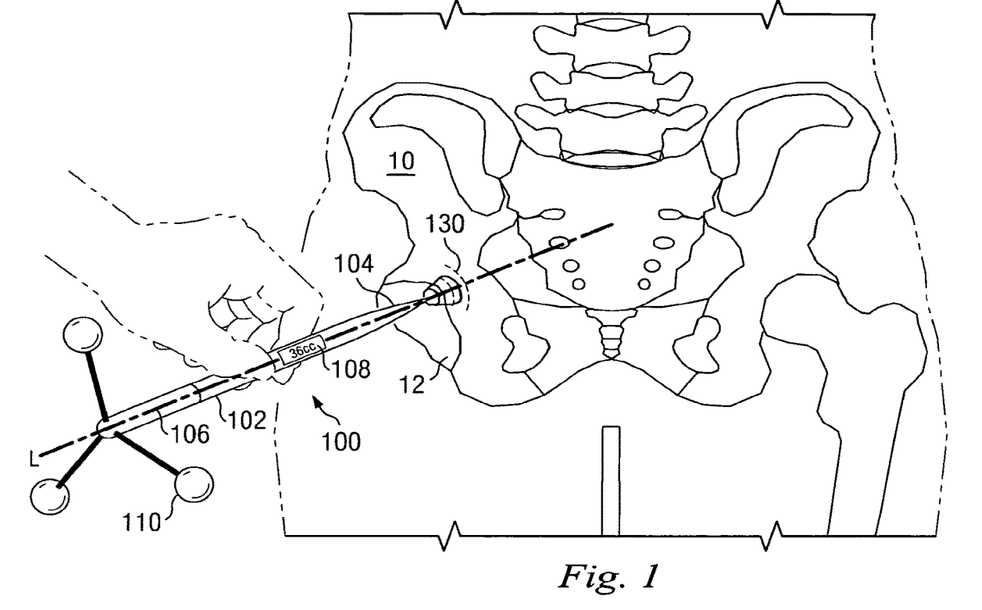
FIG. 1 is a front view of electronic instrument according to one embodiment of the present invention in use with an acetabulum.

Referring now to FIG. 1, there is shown electronic instrumentation 100 for assessing characteristics of a tissue 10 according to one aspect of the present invention. The electronic instrumentation 100 has a main body 102, a proximal end 104, and a distal end 106. The main body 102 includes a gripping surface for grasping by the user or engagement with a further instrument. The proximal end 104 is adapted for placement adjacent a surface 12 of the tissue 10 being assessed when the electronic instrumentation 100 is in use. Thus, the distal end 106 is disposed distally to the tissue being assessed when the electronic instrumentation 100 is in use. The electronic instrumentation 100 of FIG. 1 also includes a display 108 and a fiducial marker assembly 110. The fiducial marker assembly 110 is joined to distal end 106. A longitudinal axis L extends along at least a portion of the main body 102.

The main body 102 is adapted for housing the various electronic components of the electronic instrumentation 100. In FIG. 1, the main body 102 is shown as being substantially cylindrical and elongated. This is merely for illustrative purposes. It is fully contemplated that the main body 102 may take any shape capable of holding the components of the electronic instrumentation 100, including non-cylindrical and non-elongated designs. However, it is preferred that the main body 102 be of appropriate shape and size to be portable and handheld. For example, but without limitation, the main body may be of similar design, shape, and size to an injector gun, laser pointer, or pen. Still further, in another embodiment the main body 102 is narrow like a catheter or needle and is manipulated remotely for minimally invasive surgery.

Figure 3:
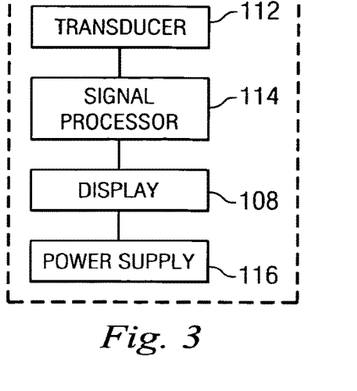
FIG. 3 is a schematic illustration of an electronic instrument according to one embodiment of the present invention.

As shown in FIG. 3, the electronic instrumentation 100 includes an acoustic transducer 112, a signal processor 114, a display 108, and a power supply 116. The acoustic transducer 112 is adapted for emitting and detecting acoustic signals. In this regard it is contemplated that the acoustic transducer 112 may function as a pulse-echo transducer having a single element for emitting and receiving acoustic signals. In that regard, the acoustic transducer 112 includes an energy source for producing or emitting the signal 130 and a sensor for detecting the echo or reflecting signal 132. The function of the energy source and the sensor may be performed by a single element or component switched between a transmit mode and a listen mode. On the other hand, the acoustic transducer 112 may be a dual-element transducer where a first element is configured for emitting acoustic signal 132 and a second element is configured to receive or detect acoustic signals 132. It is fully contemplated that the acoustic transducer 112 may be piezoelectric. It is to be understood that acoustic signals are a form of transmitted energy. It is contemplated that in an alternative embodiment other forms of energy and different frequencies are used, such as lasers, visible light, radio frequency, microwaves, etc., provided they can be transmitted into the lesion and/or tissue. For instance, the acoustic signal disclosed in the present embodiment is in the frequency range of ultrasonic signals. In some high resolution systems of the present invention, the frequency can range from 20 KHz up to and exceeding 300 MHz. For example, these frequencies may be used in acoustic microscopic instruments applications. In one aspect of the present invention, the frequency range is between 1 MHz to 15 MHz. Still further, the energy source may be any source capable of transmitting energy into the tissue that may be affected to represent tissue characteristics. For example, the energy source may utilize RF energy in the range from 400 KHz up to 10 GHz. Still further the energy source could utilize a light source generating non-coherent and/or coherent (laser) light.

The acoustic transducer 112 is adapted for placement at the proximal end 104 of the electronic instrumentation 100. In fact, the acoustic transducer 112 may itself substantially form the proximal end 104 of the electronic instrumentation 100. The acoustic transducer 112 is adapted for placement at the proximal end 104 such that when the electronic instrumentation 100 is in use the transducer can emit an acoustic signal or other type of energy wave into the tissue 10 and/or lesion 20 being monitored and receive an echo or return signal from the tissue. The proximal end 104 may include a conductive surface. Conductive surface in this context does not require, but may include electrical conductivity. Rather, conductive surface in this context is intended to mean a surface configured to facilitate the emitting and receiving of the acoustic signals. Thus, the surface may serve as the transducer to emit or receive the signal, or the surface may simply be transmissive allowing the signals to pass through. Moreover, in one aspect the conductive surface is formed as a disposable sheath such that it is discarded after each use and the instrument housing with sensing hardware is reused.

The strength and frequency of the acoustic signal can be varied depending on the type of tissue being evaluated. Further, the strength and frequency of the signal may be varied to enhance the accuracy of evaluation of a lesion boundary. For instance, the instrument may evaluate the lesion void with energy beams with multiple frequencies and then integrate the sensed information to best approximate the size or location of the void. Further, the energy beam or signal may be shaped for optimum performance and may include a focused beam, for example a beam with a substantially cylindrical or conical shape.

Figure 2:
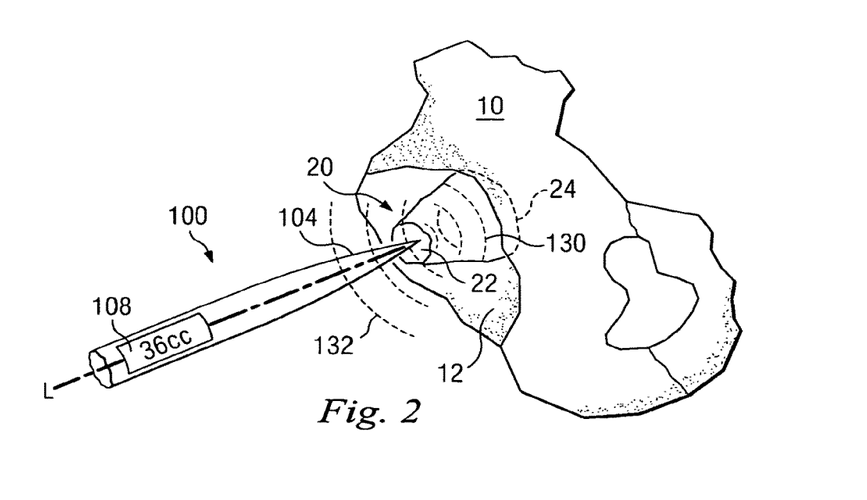
FIG. 2 is an enlarged front view of the electronic instrument of FIG. 1 in use with the acetabulum.

Consider the case of an osteolytic lesion 20 of the acetabulum 10, as shown in FIGS. 1 and 2. The proximal end 104 and the acoustic transducer 112 of electronic instrumentation 100 are placed in conductive contact with at least the exterior surface 22 of the osteolytic lesion 20. In this way conductive contact implies that the proximal end or lesion end of the instrument 100 is in sufficient contact, either direct or indirect, with the lesion to emit an acoustic signal or beam into the lesion and receive a reflected acoustic signal from a boundary 24 between the lesion and the healthy bone. In one aspect, the proximal end 104 is in direct contact with the osteolytic lesion 20 or in indirect contact via a coupling medium. Where the osteolytic lesion 20 or other tissue being monitored is located within the acetabulum 10 or other tissue, the electronic instrumentation 100 is formed of appropriate shape and material to pierce through the acetabulum 10 or otherwise become in conductive contact with the osteolytic lesion 20. The exterior surface 22 of the osteolytic lesion 20 may substantially coincide with engagement surface 12 consisting of healthy bone.

In one embodiment, the reflected energy is used to calculate first points indicating a lesion boundary and saved in memory. The sensor is moved to a different location with respect to the lesion or the orientation of the sensor is changed relative to the original position. In the new position, a series of second points based on reflected signals may be calculated and saved in memory. These first and second points are combined and used to approximate the boundary of the lesion and to approximate a volume based on the points defining the lesion boundary. Further, in one approach, the points are compared to one or more known geometric shapes of known volume to determine the best fit and thereby determine the best approximation of the volume of the lesion. For example, but without limitation to other shapes, the geometric shapes include spheres, cylinders, cubes, pyramids and cones. Further, more than one shape of different sizes may be used to approximate the lesion shape and volume. For example, a series of small cubes may be stacked in virtual space within the void boundaries to closely approximate the actual sensed volume.

The acoustic transducer 112 emits an acoustic signal 130 into the osteolytic lesion 20 through exterior surface 22. The acoustic signal 130 will pass through the lesion 20 until it arrives at the interface between the lesion and healthy bone, illustrated by boundary 24. At that point, a portion of the acoustic signal will reflect off of the boundary 24. This reflection is the echo or return signal 132 that will be received by the acoustic transducer 112. In one embodiment, based on the time delay of the return signal 132 and the assumed constant speed of the acoustic signal in the lesion, the depth of the osteolytic lesion 20 may be determined by the signal processor 114. Further, determining the depth at a variety of points or angles allows the signal processor 114 to determine the approximate volume of the lesion 20. As described more fully below, the process for determining the size or volume of the lesion 20 may range from a single pulse-echo reading, a plurality of pulse-echo readings, pulse-echo readings accompanied with position data, or other means of determining volume. It should be noted that determining volume is intended to include approximations and estimations of actual volume. Further, determining volume may be based not on the approximate volume of the lesion, but based on the corresponding bone filler required to fill the void when the lesion is removed.

Figure 4:
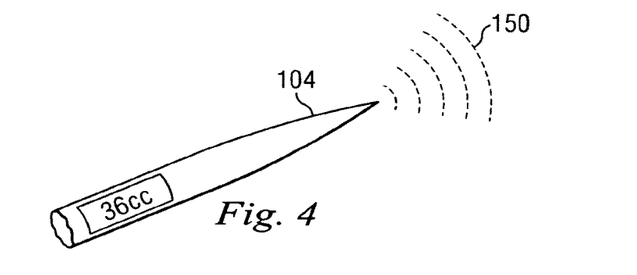
FIG. 4 is a perspective view of an electronic instrument according to one embodiment of the present invention with a substantially fan-shaped acoustic signal.

While the electronic instrumentation 100 may obtain useful tissue data from a single pulse-echo reading, such as the approximate size of the lesion 20, it is contemplated that the electronic instrumentation may be rotated about its longitudinal axis L to sequentially assess the lesion. In this respect, it is contemplated that the transducer 112 may be adapted to produce an acoustic beam with an appropriate shape for determining lesion size. For example, as shown in FIG. 4 the beam 150 may be substantially fan shaped. Where the beam is fan shaped it may be adapted for detecting the size of the lesion 20 in only a single plane, corresponding to the plane of the beam. In this case, the electronic instrumentation 100 may be rotated sequentially through a series of angles obtaining readings at each angle. In this way, the electronic instrumentation 100 may obtain one and two dimensional measurements and then based on those measurements estimate the volume of the lesion 20. It is contemplated that the instrument can also be moved along the longitudinal axis of the instrument to take a series of measurements within the void or lesion. For example the proximal end 104 may be moved from a first sensing point at surface 22 of the lesion 20 to along the longitudinal axis until the proximal end engages boundary 24 for a final sensing measurements. As the sensing portion of the instrument is moved longitudinally within the lesion or void, non-symmetrical aspects of the lesion will be sensed that may have otherwise been in shadow from other structures if the measurements were taken from only a single location. For this type of application, the energy beam or series of beams may project outwardly at least partially transverse to the longitudinal axis of the instrument or sensing region. In this way, the entire void may be more fully and completely assessed and the volume approximated.

In at least one embodiment the electronic instrumentation 100 is adapted for rotation about the longitudinal axis L to obtain readings at a plurality of angles. The more readings obtained at different angles, the more accurate the sensed data. For example, in one embodiment the electronic instrumentation 100 is rotated through 360 degrees about the longitudinal axis to obtain data. Still further, measurements are taken at a set number of angles. For example, where two measurements are taken it may be advantageous to obtain readings at a first angle and then at a second angle, where the second angle is approximately 90 degrees offset from the first angle. For another example, where three measurements are taken, readings may be obtained at a first angle, then at a second angle approximately 45 degrees offset from the first angle, and then at a third angle approximately 45 degrees offset from the third angle. Moreover, one or more rotations may be conducted at a first longitudinal position, the proximal end 104 advanced and another series of rotations may be conducted to assess the surrounding tissue. These exemplary angles are for illustration purposes only. It is fully contemplated that in alternative embodiments electronic instrumentation may obtain data from any number of different angles.

An accelerometer or gyroscope may be utilized to help determine the amount of rotation performed or indicate to the electronic instrumentation 100 when to stop taking readings. For example, the electronic instrumentation 100 may start obtaining readings and continuing obtaining readings as it is rotated about the longitudinal axis L. Once the accelerometer or gyroscope detects that the electronic instrumentation 100 has made a full 360 degree rotation it may automatically stop the readings or emit a signal, such as an audible beep, to the operator to stop obtaining readings. Then based on the data obtained over the range of angles, the electronic instrumentation can provide an accurate assessment of the lesion, including such things as three-dimensional size, shape, and location.

Further, in combination with, in addition to, or in lieu of an accelerometer or gyroscope the electronic instrumentation 100 may utilize fiducial marker assembly 110. Fiducial markers can enhance the readings obtained by the electronic instrumentation 100 by providing precise location information for the tissue. U.S. Pat. No. 6,235,038 issued to Hunter et al. and assigned to Medtronic Surgical Navigation Technologies includes disclosure regarding the use of fiducial markers and is incorporated herein by reference in its entirety. The fiducials may be of any appropriate type including optical reflectors, electrical coils, transmitters, electromagnetic, etc. Further, their placement with respect to the sensing end may be modified to suit the particular application. In this regard, the fiducial markers 110 can even provide sufficient data to create 3-D images of the tissue. This may be especially advantageous in the case where treatment requires removal of the tissue. For example, the fiducial markers 110 can allow creation of a 3-D image or model from which the tissue may then be evacuated. A second reading may be taken using the electronic instrumentation 100 and fiducial markers 110 after debridement. Based on the second reading, the physician may determine the relative success of the removal. In this regard, using the fiducial markers 110 allows the physician to not only determine if any tissue remains, but also know precisely where any unwanted tissue remains. The doctor can note those areas that still need to be removed and then attempt to remove them. This process can be repeated until the tissue is removed to the surgeon's satisfaction. This allows for successful removal of all of the undesirable tissue, which in the case of osteolytic lesions has been difficult to determine in the past.

The sensor data from instrument 100 may be transmitted to an image guided surgery (IGS) system such that the data sensed by the instrument concerning the tissue properties and three-dimensional void boundaries may be integrated with the positioning data of the IGS system. Thus, a composite three-dimensional image showing tissue type and/or void boundaries is calculated and may be displayed separately or as part of a composite image with the IGS display. The data from instrument 100 may be transmitted wirelessly or by wired communication. Alternatively, instrument 100 may include a memory for recording the sensed data. A port, such as a USB port, may be provided to connect the instrument to the IGS or other computer system to download the sensed data. In a further embodiment, the instrument 100 is a component of an IGS system. In this embodiment, sensor 100 is utilized to map the three-dimensional void boundaries and the three-dimensional location of the lesion relative to the patient's body. The IGS system then guides the user to remove all or substantially all of the lesion based on the sensed data. In an alternative system, the IGS system includes an automated bone removal device in communication with the IGS system. The automated bone removal device is advanced to the lesion site under computer control, activated to remove the lesion under computer control and removed from the lesion site. In a further aspect, the IGS system automatically locates the lesion void after debridement and fills the void with a filler material. Further, in one aspect a sensor is placed in the filler material to verify complete filling.

Where the electronic instrumentation 100 is utilized to check the removal of the lesion 20 after debridement, a coupling media is used to fill the void left by the removed lysis. For example, in one embodiment the void is filled with a saline solution or another conductive substance such that the electronic instrumentation 100 may detect the boundaries between the saline and the lesion 20 to determine if the lesion has been fully removed. In one aspect, the coupling media is a flowable material with known acoustic properties that are easily distinguishable from the lysis and surrounding bone. For example, but without limitation to other materials, the coupling media includes saline solution, blood, plasma, bone paste, bone wax, allograft, autograft, demineralized bone, BMP in a carrier matrix, mineralized granules, and bone cement. In an additional aspect, instrument 100 is used to detect proper packing of the completely debrided void with bone filler material disposed between the bone filler material and the boney boundary. The instrument may detect voids and foreign materials. In still a further embodiment, the sensing instrument 100 is provided in combination with a tamp on the proximal end. In use, this embodiment allows the surgeon evaluate the backing of material in the void and apply pressure with the tamp force filling material into sensed voids.

Figure 5:
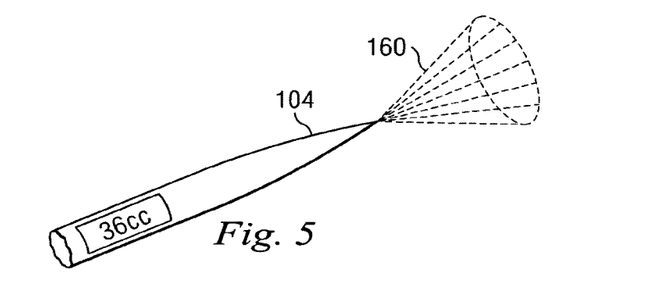
FIG. 5 is a perspective view of an electronic instrument according to one embodiment of the present invention with a substantially conical acoustic signal.
Figure 6:
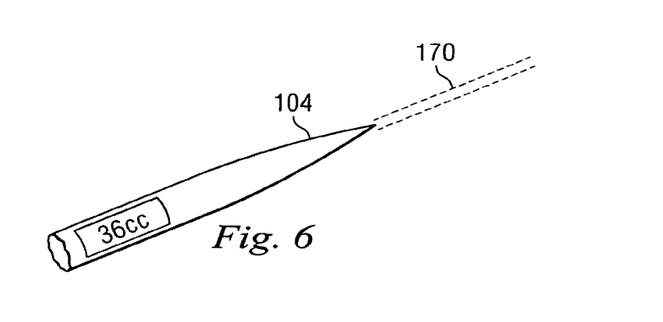
FIG. 6 is a perspective view of an electronic instrument according to one embodiment of the present invention with a focused beam acoustic signal.

In other embodiments, the acoustic beam produced by the transducer 112 may be of any shape to facilitate obtaining data from the tissue, including but not limited to substantially conical or cylindrical shapes. As shown in FIG. 5, the beam may be substantially cone shaped. Use of a cone shaped beam is advantageous when a minimal number of readings is wanted as more data can be obtained from a cone shaped beam as compared to the fan shaped beam previously described. In this regard, where the electronic instrumentation 100 is adapted to determine the approximate size of an osteolytic lesion in a single pulse-echo reading, it is contemplated, but not required, that a cone shaped beam may be utilized. As shown in FIG. 6, in one embodiment the acoustic beam is a focused beam of substantially cylindrical shape. Further, it is contemplated that a single transducer or multiple transducers within the electronic instrumentation may be capable of producing various types of beams depending on the type of tissue being examined. The treating physician may have the ability to choose the appropriate beam on a case-by-case basis. Although not shown in FIGS. 5 and 6, in another embodiment the beam is directed substantially perpendicular to the longitudinal axis of the instrument such that is senses the lesion or void to the side of the instrument.

In still a further embodiment, the instrument 100 includes a reinforced, pressure sensitive tip at proximal end 104 to probe into the lesion or void either alone or in combination with the energy source. The tip can be used to evaluate the abnormal tissue and probe the boundaries to verify the location and quality of the boundary. For instance, the bone between adjacent pockets of lesion or tumor material may be breached by the reinforced tip 104. The tip may include a pressure sensor to detect and provide a signal indicative of the amount of force applied to provide the user with feedback as to the type and integrity of the tissue being encountered. In one form, the instrument provides a proprioceptive (tactile) response to the user based on the pressure sensor and/or transducer sensor data to indicate to the user in an intuitive manner the type of tissue being encountered. In a further form, the instrument 100 includes one or more forward looking sensors that alert the user through proprioceptive response of nearing collisions with other implants or vital tissues, such as nerves and blood vessels in the vicinity. In this type of embodiment, the instrument 100 has sufficient rigidity and durability to mobilize and penetrate weak tissue such as osteolytic lesions and cancerous tumors. Alternatively, for less defined lesion boundaries, reflected energy signals may be processed to determine a gradient profile for the transitional tissue between the healthy bone and the homogenous lesion material to determine bone integrity or condition. Information from the reflected signals and/or the signals of the pressure sensitive tip is used to by the health care provider to determine the extent of debridement desired to obtain sufficient lesion removal for a successful procedure. In one form, the system may evaluate the boundary of the lesion to determine the gradient between the natural healthy tissue well outside the lesion, the substantially homogeneous lesion material and transitional tissue of potentially compromised tissue extending between the lesion and the healthy tissue. In one form, the system is programmed to select a debridement and volume boundary where the transitional tissue gradient is between 100% and 50% healthy tissue. In another form for cancerous lesion removal, the system is programmed to set the debridement boundary so it includes a buffer of healthy tissue outside of the sensed lesion boundary to ensure that all of the cancerous and pre-cancerous cells are removed.

Figure 7:
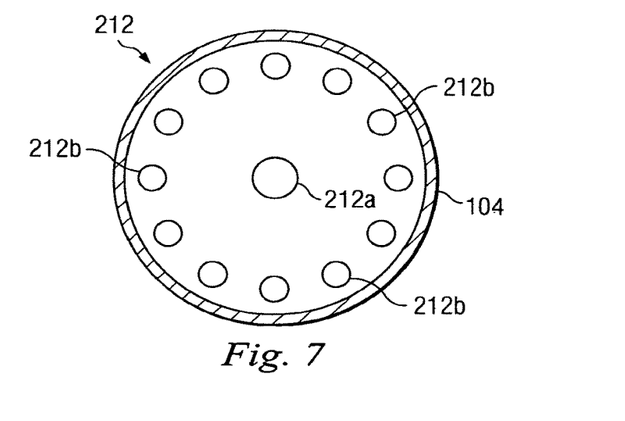
FIG. 7 is a partial cross-sectional view of a portion of an electronic instrument according to one embodiment of the present invention.

As shown in FIG. 7, it is also contemplated that in yet another embodiment that instead of rotating the electronic instrumentation 100 through a series of angles, the electronic instrumentation may include an array of transducers 212 located adjacent the proximal end 104 and disposed radially around the longitudinal axis. Where the array of transducers 212 is present there is a dedicated receiving transducer 212a for detecting the echo from the array of emitting transducers 212b. Each of the emitting transducers 212b may emit a acoustic signal at a different frequency to allow the receiving transducer to distinguish between return signals. In an alternative design, the array 212 is phased or timed such that the receiving transducer 212a is detecting a single echo at a time correlated to a single emitting transducer 212b. To this end, it is fully contemplated that the electronic instrumentation 100 includes a timing means for synchronizing the emitting and receiving of acoustic signals.

The electronic instrumentation 100 includes a display 108. The display 108 is shown in FIGS. 1 and 2 as being a liquid crystal or other type of visual display. As shown, the display 108 may be adapted to show the estimated size of the lesion, such as 36 cc. For example, but without limitation to detecting smaller or larger lesions, it is contemplated that the electronic instrumentation 100 detects lesion sizes ranging from 5 cc-100 cc. In many situations, it will not be necessary for the electronic instrumentation 100 to calculate or display to the precise volume of a lesion. In those situations, the electronic instrumentation and the display are adapted to show an indication of the general size of the lesion, such as small, medium, large, or extra large. Each size will have a corresponding range of volumes and possibly an associated surgical kit based on the amount of grafting material required. In such a case, the display 108 may be adapted to show a color, an appropriately sized bar, or a letter (e.g. S, M, L, or XL) corresponding to the size of the lesion. There are obviously any number of visual displays that may be used to indicate the size or other data readings of the electronic instrumentation 100. In at least one embodiment, the electronic instrumentation 100 is adapted to create a 3-D image of a void or lysis. In such an embodiment, the display 108 may be adapted to show the 3-D image. In addition, it is fully contemplated that the electronic instrumentation 100 not include a display.

In lieu of or in addition to display 108, alternative embodiments of the electronic instrumentation include other means of outputting tissue data in human intelligible form. For example, the instrumentation includes an audible output, such as a speaker, adapted to provide information to the caretaker. In one embodiment, the audible output beeps or makes other sounds indicating the general size of the lesion or other tissue malformity. Again, in one aspect the size of the lesion is grouped based on a kit size related to the amount of grafting material required, such as autograft, allograft, osteoconductive, or osteoinductive materials. Other human intelligible forms, such as vibrations, are also contemplated as means of outputting tissue data. For example, but without limitation, in one aspect the void is filled with a mixture of bone morphogenic protein (BMP) carrier matrix and mineralized granules. The carrier is a collagen sponge or paste including bi-calcium phosphate. The BMP may be included in a platelet gel or may be recombinant BMP. The mineralized granules are a homogenous substance or mixture of autograft, allograft, xenograft, hydroxyl appetite, bi-calcium phosphate, coral or other materials suitable for implantation. In one aspect a small kit would be a small INFUSE® bone graft kit from Medtronic, Inc. containing a 2.5 mm collagen sponge and a vial of BMP to reconstitute in solution of 1.5 mg/ml of saline solution. A medium INFUSE® bone graft kit would contain a 5.6 mm collagen sponge and a larger vial of BMP, while a large INFUSE® bone graft kit would contain a 8.0 mm collagen sponge and a larger vial of BMP to reconstitute a solution at 1.5 mg/ml of saline solution.

As shown in FIG. 1, the electronic instrumentation 100 may also be adapted for wireless communication with an external device 50. In this regard, the electronic instrumentation 100 is configured to transfer data using RFID, inductive telemetry, acoustic energy, near infrared energy, "Bluetooth," or computer networks. The electronic instrumentation 100 transfers data wirelessly to offload tasks such as the computing performed by the signal processor, displaying the data, or storing the data. Alternatively, the instrument may include a memory and have a port for transferring data. It is also contemplated that the electronic instrumentation 100 be adapted for wired communication.

The electronic instrumentation 100 includes a power supply 116. In one embodiment, the power supply 116 may be an internal power source. That is, the power supply 116 may be fully disposed within the electronic instrumentation 100. The internal power source may be a battery or a plurality of batteries. However, in an alternative embodiment it is also fully contemplated that the electronic instrumentation 100 may be adapted to receive power from an external source. For example, it is fully contemplated that the electronic instrumentation 100 receives power from a wall socket or other common power source through a wired connection. To this end, the electronic instrumentation 100 may itself include a wire adapted to plug into the power source. On the other hand, the electronic instrumentation 100 may include an adapter or receiver for selectively connecting to a wired power supply, such that the instrumentation is not permanently attached to the wire. In these embodiments, it is contemplated that the electronic instrumentation 100 receives power via a Universal Serial Bus ("USB") system. In this way the electronic instrumentation 100 may be adapted to communicate over a USB cable with an external device, such as a laptop or desktop computer, to receive power and also transmit data. The electronic instrumentation 100 utilizes the computing power of the external device to perform the signal processing and display functions. In this regard, it is contemplated that the external device may also be a handheld device such as a cell phone, PDA, BlackBerry, or similar type device. It is fully contemplated that the electronic instrumentation 100 may be configured to include as few parts as needed, utilizing the features of the external device to the full extent possible. This can be very beneficial where the electronic instrumentation 100 is adapted to be disposable such that cost is kept to a minimum.

In still a further embodiment, it is contemplated that the electronic instrumentation 100 is adapted for placement within or in combination with a tissue removal instrument or other medical device. For example, placement within or in combination with an instrument, such as a curette, brushes, burrs or laser tissue ablation device, may be particularly advantageous where the instrument is used to remove an osteolytic lesion and the electronic instrumentation 100 is utilized to determine the effectiveness of the removal by detecting any remaining lytic bone. However, in one aspect the electronic instrumentation 100 serves this same function without being disposed within the curette. To the extent that the electronic instrumentation is used in combination with another medical device, it is contemplated that the electronics are incorporated into a sheath, film, or other type of casing designed to engage the medical device without impairing the function of the medical device. In still a further embodiment, instrument 100 is incorporated with or into a minimally invasive surgical system. For example, in this embodiment the sensing features of the present system are added to powered abrader and cutters such as the Visao® High Speed Otologic Drill and XPS®, Magnum®, Straightshot®, Microdebriders offered by Medtronic Xomed, Inc. The sensor of instrument 100 would be positioned adjacent the proximal cutting end of the cutter and in one aspect, extend proximally beyond the cutter. The tissue removal device may utilize ultrasound to ablate tissue as disclosed in U.S. Pat. No. 6,692,450 to Coleman incorporated by reference herein in its entirety. In another aspect the tissue sensing device is utilized with blind cutting instruments having their cutting elements disposed out of the line of sight from the user. For example, the sensing element is placed on the angled portion of the cutting instruments disclosed in U.S. Pat. No. 6,544,749 to Mitusina, et al, incorporated by reference herein in its entirety. In still another embodiment, the tissue sensing feature of instrument 100 is combined with a lens or camera (not shown) for visualization of tissue adjacent the proximal (cutting end) of the tissue removal device. In this embodiment, the tissue sensing device provides feedback concurrently with the video image displayed by the camera to offer the surgeon additional information on tissue type and location. In yet a further embodiment, the instrument provides a proprioceptive (tactile) response to the user based on the sensor data to indicate to the user in an intuitive manner the type of tissue being encountered proximal the tissue removal device. In a further form, the instrument 100 includes one or more forward looking sensors that alert the user through proprioceptive response of nearing collisions with other implants or vital tissues, such as nerves and blood vessels in the vicinity of the tissue removal device. For example, but without limitation, the proprioceptive signals may include vibrations, lights, sounds alone or in combination. Further, each of these signals may be controlled to become more intense as the distance between the tissue removal device and vital tissue decreases indicating an imminent danger of collision. Further, when combined with an IGS system, the sensed data may be incorporated into an image display to assist the surgeon in guide the instrument to avoid vital tissues.

It is fully contemplated that the electronic instrumentation 100, whether used as a stand-alone unit or in combination with another medical device, may be disposable. That is, the electronic instrumentation 100 is designed for use in only one medical procedure or for a limited amount of time. For example, in one aspect the electronic instrumentation 100 includes a circuit that breaks or disconnects if the instrumentation is subjected to autoclaving or other types of sterilization procedures. The electronic instrumentation 100 may also include a battery with a predetermined life. For example, the battery may be designed to provide power to operate the electronic instrumentation for 8 hours after initiation. This would give the electronic instrumentation sufficient power for long surgical procedures, yet limit the useful life of the instrumentation to single use applications.

Though the electronic instrumentation has been described primarily in connection with detecting the size of lesions in bone and determining whether removal of the lesion was successful, the electronic instrumentation according the present invention has many other applications. In one application, the instrument 104 is used after filling of the void with bone filling material to evaluate completeness of the filling. For example, the difference in material properties between the native bone, the bone filler and any substance left in the void can be sensed by the instrument. If a foreign substance, such as blood, air, saline solution, lesion, tumor, etc., remains after filling the instrument may detect it and alert the user.

In another application, the electronic instrumentation is configured to determine the actual density of tissue, rather than simply distinguishing between different types of tissue. This may be advantageous in the treatment of patients with osteoporosis. In this aspect, the electronic instrumentation is adapted to determine the size of other tissue features, both good and bad. Although lesion has often been referred to in regards to an osteolytic lesion, lesion is intended to include any type of abnormal tissue, malformation or wound related to a bone or other tissue, including cancers, voids, tumors, missile injuries, projectiles, puncture wounds, fractures, etc. For example, it is fully contemplated that the disclosed electronic instrumentation is useful to detect and determine the size of bone cancer voids, cancer cells, and tumors. In another aspect, the electronic instrumentation is used to probe suspect tissue and alert the user to the presence of anomalous tissue based on reflected energy indicating different densities. In still a further aspect, the electronic instrumentation is used to monitor the growth and healing of soft tissues, such as tendons and ligaments, as well as bone. In yet a further embodiment, the electronic instrumentation is inserted into the body and energized to detect the presence of foreign bodies, such as bullets, nails, glass, or other objects, in various types of tissue and particularly associated with penetration wounds. In one embodiment, the sensor is combined with a grasping instrument such that detected foreign bodies may be located, grasped by the instrument and withdrawn from the patient. The electronic instrumentation is also used to evaluate the tissue based on the characteristics of the ultrasound signals received. In this regard, the electronic instrumentation is used to monitor bone growth or healing. As explained above, in one aspect the electronic instrumentation is employed to determine the effectiveness of tissue removal, such as evacuation of an osteolytic lesion. Further, in another aspect the electronic instrumentation is utilized to create a 2-D or 3-D image of the tissue. Finally, the electronic instrumentation may be configured to perform a plurality of these applications in combination.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of treating osteoporosis in a bone tissue, comprising:
    placing a hand-held device at least proximate a surface of the bone tissue, the hand-held device comprising multiple emitting transducers, a dedicated receiving transducer, and a processor, each of the multiple emitting transducers being configured for emitting at least one acoustic signal into the bone tissue, and the dedicated receiving transducer being configured for receiving an echo corresponding to each of the at least one acoustic signals;
    emitting, by each of the multiple emitting transducers, the at least one acoustic signal into the bone tissue, each of the at least one acoustic signal being reflected by a boundary of an osteoporotic region of the bone tissue as an echo;
    detecting, by the dedicated receiving transducer, each of the echoes corresponding to each of the at least one acoustic signals;
    determining, by the processor, a time delay for each of the detected echoes;
    determining, by the processor, boundaries of the osteoporotic region by calculating depths thereof based on the determining of the time delays and assumed speeds for each of the at least one acoustic signals;
    determining a location of the osteoporotic region in the bone tissue using the determined boundaries;
    determining, by the processor, an approximate volume of the osteoporotic region based on the determined boundaries of the osteoporotic region and comparing the determined boundaries to one or more geometric shapes of known volume; and
    utilizing the location and the approximate volume of the osteoporotic region to guide a surgical instrument to the osteoporotic region.

2. The method of claim 1, further comprising delivering at least one of autograft, allograft, osteoconductive material, osteoinductive material, and bone morphogenic protein via the surgical instrument to the osteoporotic region.

3. The method of claim 1, wherein each of the multiple emitting transducers is configured to emit the at least one acoustic signal at at least one of a plurality of different frequencies.

4. The method of claim 3, wherein the plurality of different frequencies include frequencies in a range between 15 KHz and 100 MHz.

5. The method of claim 3, wherein the plurality of different frequencies include frequencies in a range between 20 KHz to approximately 20 MHz.

6. The method of claim 1, wherein the hand-held device includes a body portion having a first end and an opposite second end, and the multiple emitting transducers are provided at the first end.

7. The method of claim 6, wherein the first end of the body portion includes a conductive surface formed as a disposable sheath; and the method further comprising replacing the disposable sheath after each use of the hand-held device.

8. A method of treating osteoporosis in a bone tissue, comprising:
   placing a hand-held device at least proximate a surface of the bone tissue, the hand-held device comprising multiple emitting transducers, a dedicated receiving transducer, and a processor;
   emitting, by each of the multiple emitting transducers, at least one acoustic signal into the bone tissue;
   detecting, by the dedicated receiving transducer, an echo reflected by a boundary of an osteoporotic region of the bone tissue as an echo corresponding to each of the at least one acoustic signals;
   determining, by the processor, a time delay for each of the detected echoes;
   determining, by the processor, boundaries of the osteoporotic region by calculating depths thereof based on the determining of the time delays and assumed speeds for each of the at least one acoustic signals;
   determining a location of the osteoporotic region in the bone tissue using the determined boundaries;
   determining, by the processor, an approximate volume of the osteoporotic region based on the determined boundaries of the osteoporotic region and comparing the determined boundaries to one or more geometric shapes of known volume; and
   utilizing the location and the approximate volume of the osteoporotic region to guide a surgical instrument to the osteoporotic region.

9. The method of claim 8, further comprising delivering at least one of autograft, allograft, osteoconductive material, osteoinductive material, and bone morphogenic protein via the surgical instrument to the osteoporotic region.

10. The method of claim 8, wherein each of the emitting transducers is configured to emit the at least one acoustic signal at at least one of a plurality of different frequencies.

11. The method of claim 10, wherein the plurality of different frequencies include frequencies in a range between 15 KHz and 100 MHz.

12. The method of claim 10, wherein the plurality of different frequencies include frequencies in a range between 20 KHz to approximately 20 MHz.

13. The method of claim 8, wherein the hand-held device includes a body portion having a first end and an opposite second end, and the multiple emitting transducers are provided at the first end.

14. The method of claim 13, wherein the first end of the body portion includes a conductive surface formed as a disposable sheath; and the method further comprising replacing the disposable sheath after each use of the hand-held device.

15. A method of treating osteoporosis in a bone tissue, comprising:
   emitting, by each of multiple emitting transducers, at least one acoustic signal into the bone tissue;
   detecting, by a dedicated receiving transducer, an echo reflected by a boundary of an osteoporotic region of the bone tissue as an echo corresponding to each of the at least one acoustic signals;
   determining, by a processor, a time delay for each of the detected echoes;
   determining, by the processor, boundaries of the osteoporotic region by calculating depths thereof based on the determining of the time delays and assumed speeds for each of the at least one acoustic signals;
   determining a location of the osteoporotic region in the bone tissue using the determined boundaries;
   determining, by the processor, an approximate volume of the osteoporotic region based on the determined boundaries of the osteoporotic region and comparing the determined boundaries to one or more geometric shapes of known volume; and
   utilizing the location and the approximate volume of the osteoporotic region to guide a surgical instrument to the osteoporotic region.

16. The method of claim 15, further comprising delivering at least one of autograft, allograft, osteoconductive material, osteoinductive material, and bone morphogenic protein via the surgical instrument to the osteoporotic region.

17. The method of claim 15, wherein each of the emitting transducers is configured to emit the at least one acoustic signal at at least one of a plurality of different frequencies.

18. The method of claim 17, wherein the plurality of different frequencies include frequencies in a range between 15 KHz and 100 MHz.

19. The method of claim 17, wherein the plurality of different frequencies include frequencies in a range between 20 KHz to approximately 20 MHz.

20. The method of claim 15, wherein the multiple emitting transducers and the dedicated receiving transducer are part of an electronic instrument, the electronic instrument having a body portion including a first end and an opposite second end, the multiple emitting transducers are provided at the first end.

\* \* \* \* \*